US011585778B2

(12) United States Patent
Gao et al.

(10) Patent No.: US 11,585,778 B2
(45) Date of Patent: Feb. 21, 2023

(54) MULTIPLEXED SENSOR FOR ULTRA-FAST AND LOW-COST COVID-19 DIAGNOSIS AND MONITORING

(71) Applicant: California Institute of Technology, Pasadena, CA (US)

(72) Inventors: Wei Gao, Pasadena, CA (US); Rebeca M. Torrente-Rodriguez, Pasadena, CA (US); Heather Lukas, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 17/465,709

(22) Filed: Sep. 2, 2021

(65) Prior Publication Data

US 2022/0065807 A1 Mar. 3, 2022

Related U.S. Application Data

(60) Provisional application No. 63/073,841, filed on Sep. 2, 2020.

(51) Int. Cl.
| | | |
|---|---|---|
| *G01N 27/327* | (2006.01) | |
| *B01L 3/00* | (2006.01) | |
| *G01N 33/68* | (2006.01) | |

(52) U.S. Cl.
CPC .... *G01N 27/3277* (2013.01); *B01L 3/502715* (2013.01); *G01N 33/6857* (2013.01); *B01L 2300/023* (2013.01); *B01L 2300/0636* (2013.01); *B01L 2300/0645* (2013.01); *G01N 2333/165* (2013.01)

(58) Field of Classification Search
None
See application file for complete search history.

(56) References Cited

PUBLICATIONS

Li, X. et al. A Microfluidic Paper-Based Origami Nanobiosensor for Label-Free, Ultrasensitive Immunoassays, ADvanced Healthcare Materials, 5, 1326-1335 (Year: 2016).*

Burbelo, P.D. et al. Sensitivity in Detection of Antibodies to Nucleocapsid and Spike Proteins of Severe Acute Respiratory Syndrome Coronavirus 2 in Patients With Coronavirus Disease 2019, The Journal of Infectious Disease, 2020:222, 206-213 (Year: 2020).*

Huang, C. et al. Rapid Detection of IgM Antibodies against the SARS-CoV-2 Virus via Colloidal Gold Nanoparticle-Based Lateral-Flow Assay, ACS Omega, 5, 12550-12556 (Year: 2020).*

* cited by examiner

Primary Examiner — Xiaoyun R Xu

(57) ABSTRACT

A biosensor for the rapid, inexpensive, quantitative, and convenient detection of SARS-CoV-2 biomarkers, methods of manufacturing, and methods of using the same, to identify a patient's prognosis and past/present SARS-CoV-2 infection status, wherein the biosensor comprises a microfluidics layer, a multimodal sensing layer comprising two or more working electrodes, and a logic circuit that may include a processor and non-transitory memory with computer executable instructions embedded thereon.

17 Claims, 6 Drawing Sheets

MULTIPLEXED SENSOR FOR ULTRA-FAST AND LOW-COST COVID-19 DIAGNOSIS AND MONITORING

CROSS-REFERENCE TO RELATED APPLICATIONS

The present application claims priority to U.S. Provisional Patent Application No. 63/073,841, filed Sep. 2, 2020, the content of which is incorporated in its entirety herein by reference.

BACKGROUND

Increased access to SARS-CoV-2 testing has allowed increased monitoring of the community spread of the COVID-19 pandemic, but several diagnostic challenges remain. Currently, the standard testing method is viral nucleic acid real-time polymerase chain reaction (RT-PCR), which is a slow process and requires expensive equipment and trained technicians for nasopharyngeal swab sample collection and analysis. In addition, the sheer volume of testing required is overwhelming the ability for healthcare systems to report RT-PCR results to patients, causing, in some states, delays of 7-10 days to inform positive findings and enact isolation and monitoring protocols. Despite the recent advances on point-of-care (POC) rapid RT-PCR test, nucleic acid tests are also known to produce false negatives, which may limit containment strategies and access to treatment. An additional consideration for RT-PCR is that it only identifies active carriers of the virus. Identifying convalescent persons based on SARS-CoV-2 antibody presentation is equally important as it may provide health officials with crucial information regarding the potential impact of reopening measures. Serologic assays detect circulating antibodies specific to SARS-CoV-2 antigens, including the nucleocapsid protein and the outer spike protein. However, it is not possible to differentiate between asymptomatic carriers and immune persons using antibody detection. Therefore, to effectively mitigate the risks of SARS-CoV-2 community spread, systems are required that determine simultaneously both the viral and serologic status of an individual. Moreover, recent studies show correlation between circulating inflammatory biomarker concentration and SARS-CoV-2 severity. For example, increased C-reactive protein (CRP) concentration is found in patients diagnosed with SARS-CoV-2 pneumonia and is associated with increasing severity, suggesting a role in diagnosis and prognosis of SARS-CoV-2 patients.

While there has been progress towards POC SARS-CoV-2 testing, all commercially available test kits provide only qualitative or semi-qualitative results. Moreover, simple, safe and effective SARS-CoV-2 sample collection has proved challenging given current assay requirements.

Thus, there remains a need for a sensitive, rapid, inexpensive, quantitative, and convenient (e.g., telemedicine) methods of detection of SARS-CoV-2 that can identify a patient's past and present infection status simultaneously.

SUMMARY

The present disclosure is directed to rapid detection and quantification of biomarkers specific to SARS-CoV-2 (e.g., COVID-19) in a biological sample using a biosensor. The biosensor and methods disclosed herein enable the cost-effective, expedient, and effective data collection of SARS-CoV-2 biomarkers in a biological sample.

In one embodiment, is a biosensor capable of rapid detection and quantification of biomarkers specific to SARS-CoV-2 in a biological sample, comprising:
  (a) a microfluidics layer;
  (b) a multimodal layer comprising:
    (i) a counter electrode;
    (ii) a reference electrode;
    (iii) a first working electrode comprising a first detection protein configured to capture a first SARS-CoV-2 biomarker;
    (iv) a second working electrode comprising a second detection protein configured to capture a second SARS-CoV-2 biomarker;
    (v) a third working electrode comprising a third detection protein configured to capture a third SARS-CoV-2 biomarker; and
    (vi) a fourth working electrode comprising a fourth detection protein configured to capture a fourth SARS-CoV-2 biomarker;
  (c) a logic circuit comprising a processor and a non-transitory memory with computer executable instructions embedded thereon;
  wherein the microfluidics layer comprises multiple microchannels transversely oriented to channel a biological sample from a first surface of the microfluidics layer to a second surface of the microfluidics layer, the biological sample comprising a first, second, third, and/or fourth SARS-CoV-2 biomarker;
  the multimodal sensing layer is fluidically coupled to the second surface of the microfluidics layer to receive the biological sample from the microchannels;
  the electrodes configured to detect a measurement of an electrical property corresponding to the first, second, third, and/or fourth SARS-CoV-2 biomarkers being present in the biological sample; and
  the logic circuit is electrically coupled to the electrodes and the computer executable instructions cause the processor to identify the electrical properties detected with the electrodes when the first, second, third, and/or fourth SARS-CoV-2 biomarkers are present in the biological sample.

In another embodiment, methods of rapid detection and quantification of biomarkers specific to SARS-CoV-2 (COVID-19) in a biological sample comprises:
  (a) using a biosensor comprising:
    (i) a microfluidics layer comprising a plurality of microchannels transversely oriented to channel a biological sample from a first surface of the microfluidics layer to a second surface of the microfluidics layer;
    (ii) a multimodal sensing layer fluidically coupled to the microfluidics layer comprising:
      (1) a counter electrode;
      (2) a reference electrode;
      (3) a first working electrode comprising a first detection protein configured to capture a first SARS-CoV-2 biomarker;
      (4) a second working electrode comprising a second detection protein configured to capture a second SARS-CoV-2 biomarker;
      (5) a third working electrode comprising a third detection protein configured to capture a third SARS-CoV-2 biomarker; and
      (6) a fourth working electrode comprising a fourth detection protein configured to capture a fourth SARS-CoV-2 biomarker; and (ii) a logic circuit, the method comprising:

(b) receiving, on a first surface of the microfluidics layer, a biological sample comprising the first, second, third, and/or fourth SARS-CoV-2 biomarkers, such that the biological sample can be channeled from a first surface of the microfluidics layer to a second surface of the microfluidics layer;

(c) obtaining, with the electrodes, a measurement of an electrical property of the first, second, third, and/or fourth SARS-CoV-2 biomarkers; and (d) generating, with the logic circuit, an indication that the first, second, third, and/or fourth SARS-CoV-2 biomarkers is/are present in the biological sample based on the measurement of the electrical properties of the first, second, third, and/or fourth SARS-CoV-2 biomarkers.

Other features and aspects of the disclosure will become apparent from the following detailed description, taken in conjunction with the accompanying drawings, which illustrate, by way of example, the features in accordance with various embodiments. The summary is not intended to limit the scope of the invention, which is defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

Figure 1B:
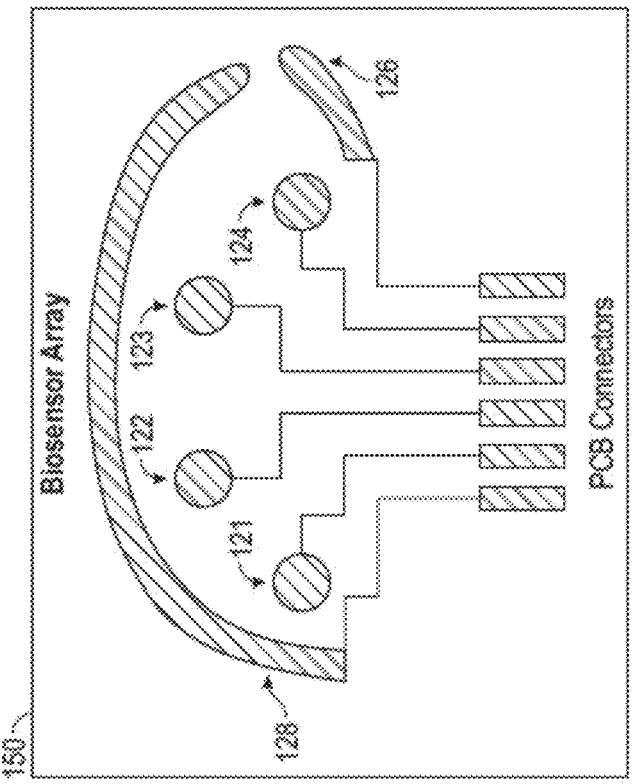
FIGS. 1A and 1B show a wireless graphene-based telemedicine platform for rapid and multiplex electrochemical detection of SARS-CoV-2 viral proteins, antibodies (IgG and IgM), and C reactive protein (CRP) in blood and saliva.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION

The following description sets forth exemplary embodiments of the present technology. It should be recognized, however, that such description is not intended as a limitation on the scope of the present disclosure but is instead provided as a description of exemplary embodiments.

On Mar. 11, 2020, the World Health Organization characterized the COVID-19 outbreak as a pandemic. Six months later, the global health crisis had continued with over 25 million confirmed cases of novel coronavirus globally—over 23% of these were in the United States. It is estimated that 14-20% of patients develop severe illness requiring hospitalization. Initial efforts to mitigate the spread through state-mandated "stay-at-home" orders appeared effective, however, reopening of the United States economy resulted in renewed exponential spread of novel coronavirus, as predicted. It is estimated that the United States gross domestic product (GDP) will suffer losses upwards of $45.3 billion during a flu-like pandemic without available vaccines. Safe reopening of the economy, schools and universities requires multiple approaches to mitigate the risks associated with COVID-19, including simple, affordable and effective test-and-trace measures.

Containing the spread of COVID-19 is difficult due to the challenges in identifying infectious individuals. Most COVID-19 community spread may occur in the absence of symptoms. Peak viremia may be at the end of the incubation period, allowing for a transmission-sufficient viral load 1-2 days prior to symptom onset. Additionally, due to the unknown duration and prevalence of asymptomatic cases, the true reproduction number may be under-estimated. Reported incidence of asymptomatic patients ranges from 17.9% to 30.8%.

In some embodiments, is a biosensor capable of rapid detection and quantification of biomarkers specific to SARS-CoV-2 (e.g., COVID-19) in a biological sample, comprising: (a) a microfluidics layer; (b) a multimodal sensing layer comprising (i) a counter electrode, (ii) a reference electrode, (iii) a first working electrode comprising a first detection protein configured to capture a first SARS-CoV-2 biomarker, and (iv) a second working electrode comprising a second detection protein configured to capture a second SARS-CoV-2 biomarker; and (c) a logic circuit with a processor and a non-transitory memory with computer executable instructions embedded thereon. In some embodiments, the multimodal sensing layer further comprises a third working electrode comprising a third detection protein configured to capture a third SARS-CoV-2 biomarker. In some embodiments, the multimodal sensing layer further comprises a fourth working electrode comprising a fourth detection protein configured to capture a fourth SARS-CoV-2 biomarker.

In some embodiments, a working electrode may comprise two detection proteins configured to capture a first SARS-CoV-2 biomarker and a second SARS-CoV-2 biomarker. In some embodiments, the working electrode may comprise a third detection protein configured to capture a third SARS-CoV-2 biomarker. In some embodiments, the working electrode may comprise a fourth detection protein configured to capture a fourth SARS-CoV-2 biomarker. In some embodiments, the working electrode is configured to detect measurements of electrical properties corresponding to the first, second, third, and/or fourth SARS-CoV-2 biomarkers being present in the biological sample. In some embodiments, the working electrode is configured to quantitate and differentiate detection of the first, second, third, and/or fourth SARS-CoV-2 biomarkers using stripping voltammetry.

In some embodiments, the microfluidics layer may comprise multiple microchannels transversely oriented to channel a biological sample from a first surface of the microfluidics layer to a second surface of the microfluidics layer.

In some embodiments, the multimodal sensing layer may be fluidically coupled to the second surface of the microfluidics layer to receive the biological sample from the microchannels. The first, second, third, and fourth working electrodes, for example, may be configured to detect measurements of electrical properties corresponding to a first, second, third, and/or fourth SARS-CoV-2 biomarker being present in the biological sample. In some embodiments, the multimodal sensing layer comprises a polymer, for example, polyimide film.

In some embodiments, the first, second, third, and/or fourth working electrodes may also include a uniform redox probe, wherein the uniform redox probe is deposited on a surface of the first, second, third, and/or fourth working electrodes.

In some embodiments, the first, second, third, and/or fourth working electrodes comprise a catalytically active substrate. In some embodiments, the catalytically active substrate is graphene.

In some embodiments, the electrical property may be an electrical current, an electrical voltage, or an electrical impedance.

In some embodiments, the reference electrode is a Ag/AgCl reference electrode. In some embodiments the counter electrode is a graphene counter electrode. In some embodiments, the counter electrode is a platinum electrode.

In some embodiments, the logic circuit may be electrically coupled to the electrodes and the computer executable instructions may include causing the processor to generate an indication identifying the presence of the first, second, third, and/or fourth SARS-CoV-2 biomarkers based on the electrical properties detected with the first, second, third, and/or fourth working electrodes. In some embodiments, the biosensor may also include a display, wherein the computer executable instructions may cause the processor to output the indication identifying the presence of the first, second, third, and/or fourth SARS-CoV-2 biomarkers to the display.

In some embodiments, the biological sample is selected from the group consisting of sweat, tears, blood, urine, saliva, and combinations thereof.

In some embodiments, the first, second, third, and fourth SARS-CoV-2 biomarkers are selected from the group consisting of SARS-CoV-2 nucleocapsid protein (NP), SARS-CoV-2 spike protein (S), SARS-CoV-2 membrane protein (M), SARS-CoV-2 envelope protein (E), immunoglobulin G against SARS-CoV-2 spike protein (S1-IgG), immunoglobulin M against SARS-CoV-2 spike protein (S1-IgM), immunoglobulin A against SARS-CoV-2 spike protein (S1-IgA), interleukin 6 (IL-6), interleukin 10 (IL-10), tumor necrosis factor alpha (TNFα), interferon gamma (IFNγ), and C-reactive protein (CRP).

In some embodiments, the methods of rapid detection of SARS-CoV-2 biomarkers use capture antigens and antibodies specific to the biomarkers of interest. In some embodiments, the capture antigens and antibodies are immobilized on the first, second, third, and/or fourth working electrodes. In some embodiments, the antibodies are enzyme-conjugated specific antibodies. In some embodiments, the first, second, third, and/or fourth SARS-CoV-2 biomarkers are molecularly detected with enzyme-conjugated specific antibodies as labeling molecules.

In some embodiments, the methods of rapid detection of the first, second, third, and/or fourth SARS-CoV-2 biomarkers use redox molecules and enzymatic substrates to detect the electrical current with the first, second, third, and/or fourth working electrodes. In some embodiments, the redox molecule may be hydroquinone. In some embodiments, the enzymatic substrate may be hydrogen peroxide.

In some embodiments, is a method of rapid detection and quantification of biomarkers specific to SARS-CoV-2 (e.g., COVID-19) in a biological sample using a biosensor. The biosensor, for example, may include: (a) a microfluidics layer that may comprise a plurality of microchannels transversely oriented to channel a biological sample from a first surface of the microfluidics layer to a second surface of the microfluidics layer; (b) a multimodal sensing layer comprising (i) a counter electrode, (ii) a reference electrode, (iii) a first working electrode comprising a first detection protein configured to capture a first SARS-CoV-2 biomarker, (iv) a second working electrode comprising a second detection protein configured to capture a second SARS-CoV-2 biomarker, (v) a third working electrode comprising a third detection protein configured to capture a third SARS-CoV-2 biomarker, and (vi) a fourth working electrode comprising a fourth detection protein configured to capture a fourth SARS-CoV-2 biomarker; and (c) a logic circuit.

In some embodiments, the methods may include: (a) receiving, on a first surface of the microfluidics layer, a biological sample comprising the first, second, third, and/or fourth SARS-CoV-2 biomarkers, such that the biological sample can be channeled from a first surface of the microfluidics layer to a second surface of the microfluidics layer; (b) obtaining, with the first, second, third, and/or fourth working electrodes, a measurement of electrical properties of the first, second, third, and/or fourth SARS-CoV-2 biomarkers; and (c) generating, with the logic circuit, an indication that the first, second, third, and/or fourth SARS-CoV-2 biomarkers are present in the biological sample based on the measurement of the electrical properties.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Example 1: Design of the SARS-CoV-2 Biomarker Detecting Biosensor Array

Figure 1A:
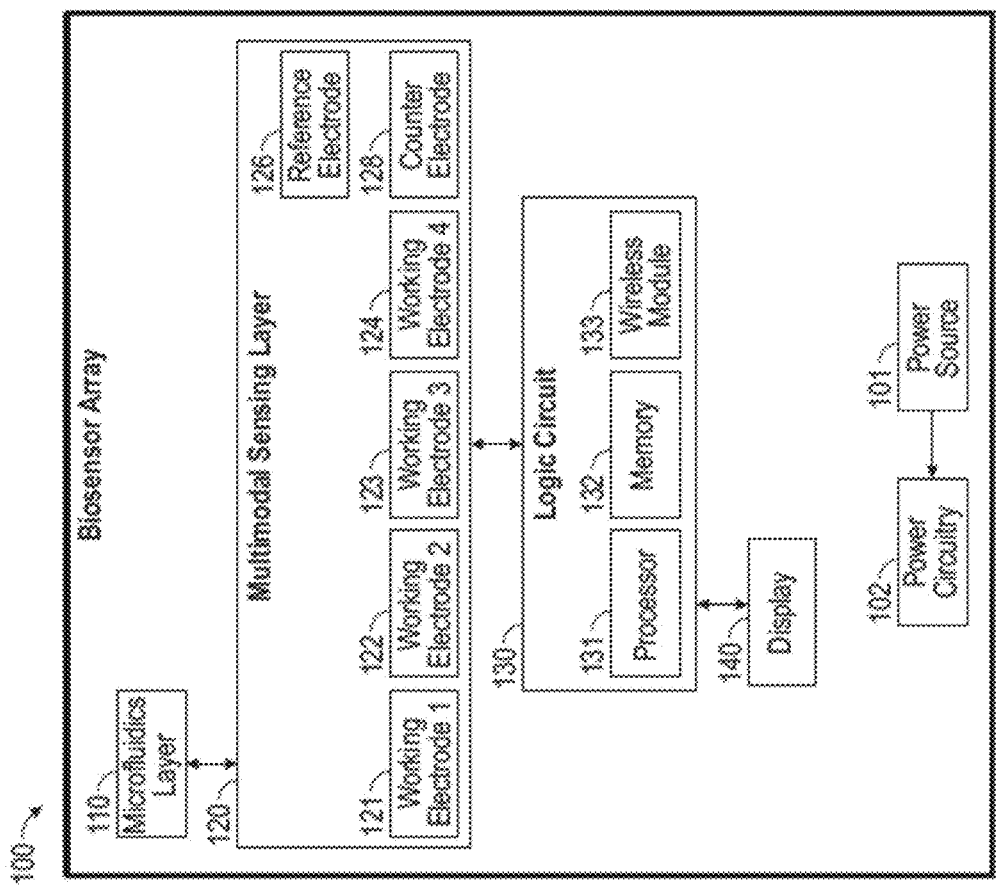

As illustrated in FIGS. 1A and 1B, a block diagram (FIG. 1A) and schematic (FIG. 1B) illustrate some components of a biosensor array 100, in accordance with various embodiments of the disclosure. The biosensor array 100 may include, for example, a microfluidics layer 110; a multimodal sensing layer 120 comprising a first working electrode (WE) 121, a second WE 122, a third WE 123, a fourth WE 124, a reference electrode (RE) 126, and a counter electrode (CE) 128; a logic circuit 130 comprising a processor 131, memory 132, and a wireless module 133; and optionally, a display 140. The electrical components of the biosensor array 100 may be powered by a power source 101 that connects the power circuitry 102 for distributing power (FIG. 1A). The power source 101 may be a battery, capacitor, or other power source known in the art. The power source 101 may be rechargeable (e.g., via a USB port and/or an AC/DC converter), and it should be appreciated that any suitable power source technologies may be used to power the components of the biosensor array 100. For example, lithium-ion batteries, cell batteries, piezo or vibration energy harvesters, photovoltaic cells, AC/DC sources, or other like devices can be used.

Figure 2:
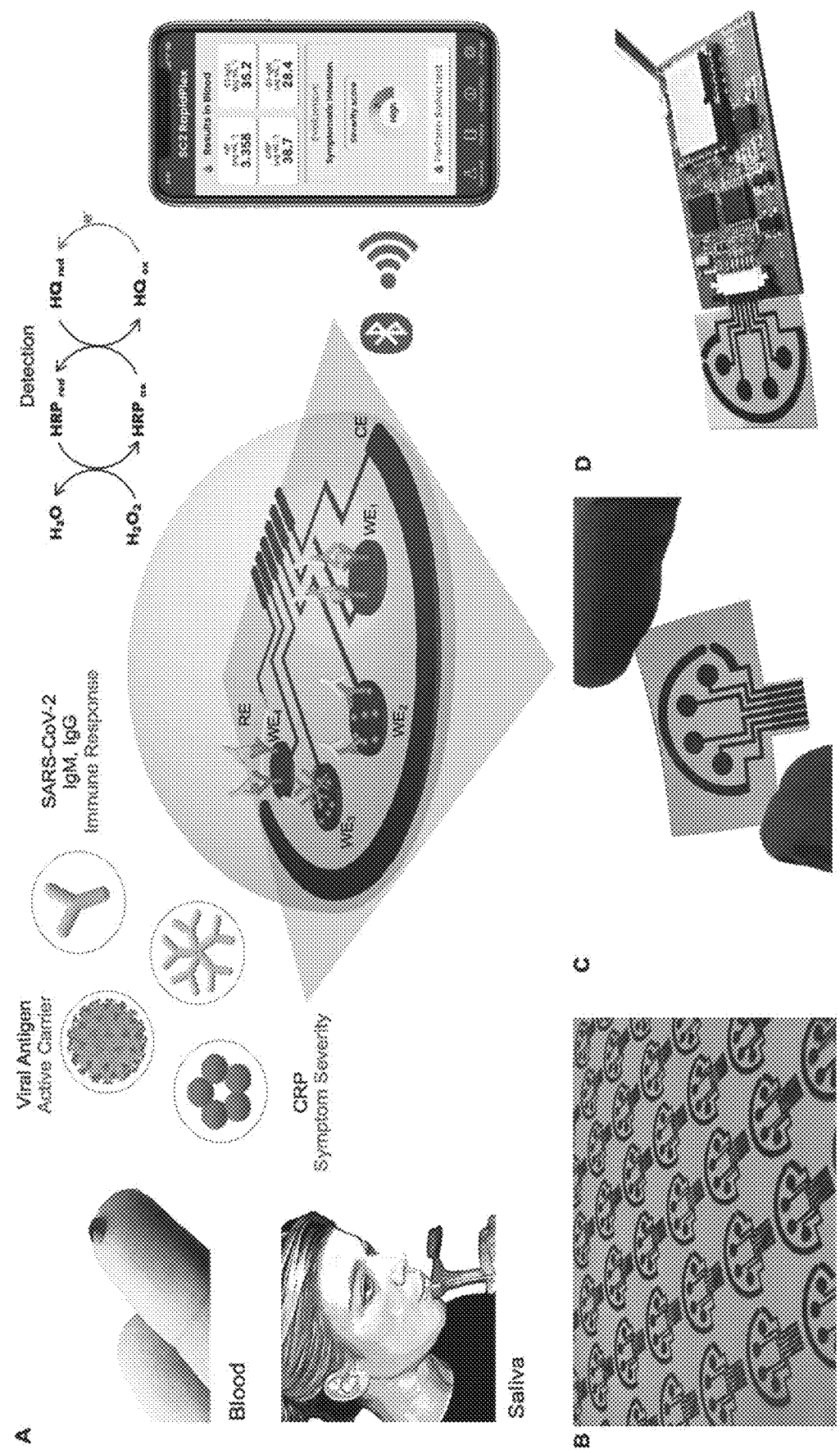
FIG. 2, panels A-E, shows characterization of electrochemical graphene biosensors comprising the SARS-CoV-2 methods of detection.

In some embodiments, the electrodes may comprise printed circuit board (PCB) connectors, connecting to a logic circuit 130 (e.g., a PCB) for signal processing and wireless communication (FIG. 1B; FIG. 2, panels A-D). The electrodes may be patterned on a polymer 150 via $CO_2$ laser engraving, a fast, high-throughput, and cost-effective production method. The first WE 121, second WE 122, third WE 123, and fourth WE 124 may be comprised of a catalytically active substrate. The catalytically active substrate may be graphene. The RE 126 may be a Ag/AgCl RE. The CE 128 may be a graphene CE.

The use of mesoporous graphene structure fabricated by laser engraving demonstrates high performance and low-cost biosensing. Detection of selected target proteins (e.g., NP and CRP) and specific immunoglobulins (e.g., S1-IgG and S1-IgM) is achieved through sandwich- and indirect-based immunosensing strategies onto the biosensor first WE 121, second WE 122, third WE 123, and fourth WE 124. The superior properties of graphene, in terms of high charge mobility and surface area together with the high sensitivity and selectivity of sensing strategies involving both capture and detector receptors, make the biosensor array 100 a highly convenient tool for the rapid, accurate, and stage-specific SARS-CoV-2 infection detection in blood as well as in non-invasive biofluid samples, such as saliva (FIG. 2, panel A).

Example 2: Electrochemical Characterization of SARS-CoV-2 RapidPlex Platform

Figure 3:
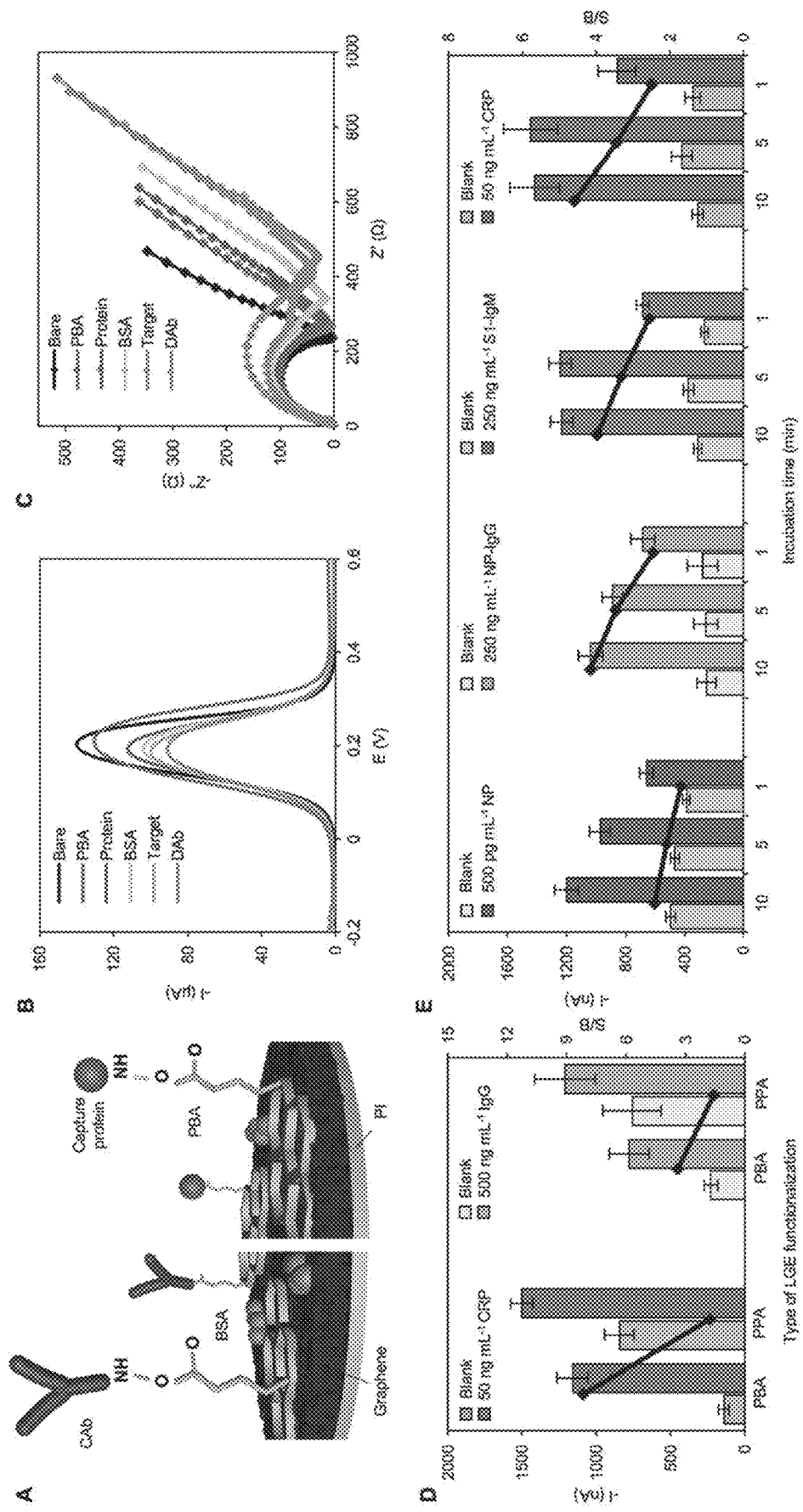
FIG. 3, panels A-F, shows evaluation of analytical sensor performance for the detection of physiological levels of target COVID-19 biomarkers.

Functionalization and modification steps carried out on the biosensor surfaces for the covalent attachment of each of the specific detection proteins required for the development of the SARS-CoV-2 RapidPlex platform is schematized in FIG. 3A. In some embodiments, 1-pyrenebutyric acid (PBA) may be used as the linker to anchor the required capture proteins to the graphene layer. In some embodiments, PBA consisting of a pyrene group that contains π-electrons and a carboxylic group may be used to functionalize graphene layers via π-π stacking and hydrophobic interactions. The functional moieties contained in each PBA molecule may be used for the fabrication of the affinity-based biosensing platform through the covalent coupling between the carboxylic groups on PBA units and the —$NH_2$ groups of the respective capture proteins (e.g., specific antibodies or capture proteins). In some embodiments, unreacted sites may be blocked to impede the non-specific adsorption of other molecules involved in each assay configuration or circulating in the biological sample. In some embodiments, unreacted sites are blocked with bovine serum albumin (BSA).

Differential pulse voltammetry (DPV) and open circuit potential-electrochemical impedance spectroscopy (OCP-EIS) techniques may be employed to electrochemically characterize and prove the stepwise self-assembled processes in both assay configurations for the detection of selected target molecules. DPV readings reflect lower peak current intensity after each modification step related to S1-Ig assay due to the hindered diffusion of the redox label to the WE surface derived from both the carboxyl groups, the attached proteins, and biological macromolecules (FIG. 3B). At the same time, resistance in the Nyquist plots from OCP-EIS is increased after each functionalization step (FIG. 3C).

To preserve the native structure and properties of the bound biomarkers, PBA was chosen as a heterobifunctional linker, effectively preventing the direct interaction between large biomolecules and the graphene surface. In order to verify this selection, CRP and SARS-CoV-2 specific IgG assay configurations were constructed on graphene electrodes functionalized with PBA and another common linker, 1H-pyrrole-1-propionic acid (PPA). Greater signal-to-blank (SB) ratios were observed for both assays where PBA was used as a linker support (FIG. 3D), mainly due to a significant decrease in the signals obtained in the absence of the corresponding target molecule when PBA was used instead of PPA. Together with an optimal blocking strategy, PBA may be used for the immobilization of specific biomolecular probes (e.g., antibodies and proteins) while avoiding non-specific adsorptions in the context of immunoassays.

The orientation of modified antigenic proteins on solid surfaces is strongly associated with their activity and reactivity. Specific anti-His antibodies can be used to orient the immobilization of antigenic receptors containing histidine residues, but this implies an additional step compared with their direct attachment on the sensing layer. Results show no significant differences in assay performance for IgG detection on graphene electrodes covalently functionalized with the specific coating protein (direct immobilization) and with anti-His antibodies for the previous capture of the polyhistidine-tag specific coating protein (oriented immobilization), proving that random protein orientation does not interfere with the epitope accessibility for effective recognition by specific target antibodies. This is in agreement with other reports confirming that His-tagged fusion antigens can be directly immobilized on different surfaces with protein orientations completely compatible with antibody recognition. In order to simplify and reduce the cost and time of the assay, direct immobilization of S1 protein was carried out for specific Ig detection.

Considering that rapid target binding is essential to the successful implementation of the platform as a POC system, we investigated how target (or sample) incubation time affects the response of each biosensor comprising the SARS-CoV-2 RapidPlex platform. FIG. 3E summarizes the amperometric signals obtained for each of the four SARS-CoV-2 biomarkers at different incubation times (10, 5, and 1 minutes) in the absence (blank, B) and in the presence (signal, S) of 500 pg mL$^{-1}$, 250 ng mL$^{-1}$, and 50 ng mL$^{-1}$ of NP, SARS-CoV-2 specific IgG and IgM isotypes, and CRP, respectively. It is important to note that although a 10-minute incubation time was selected for most of the studies here in order to ensure the highest sensitivity for the determination of ultra-low levels of each target molecule, a significant difference between the absence and the presence of each of the corresponding biomarkers is obtained with just 1-minute incubation time. This provides one of the major advantages of the SARS-CoV-2 RapidPlex system as a rapid POC device for SARS-CoV-2 infection monitoring with the required sensitivity for both protein and Ig determination. ELISA, nucleic acid amplification, mass spectrometry, or even combinations have been reported very recently for determination of the proposed SARS-CoV-2 specific target molecules, among others. However, most of these methods show crucial pitfalls, mainly in terms of sample preparation, complexity, and expensive and bulky equipment requirements, that make them still highly difficult to be implemented as POC systems. The present disclosure provides an attractive alternative to standard assays for protein determination, such as ELISA, because of its multiplexing capabilities, remote functionality, and short sample-to-answer time.

Figure 4:
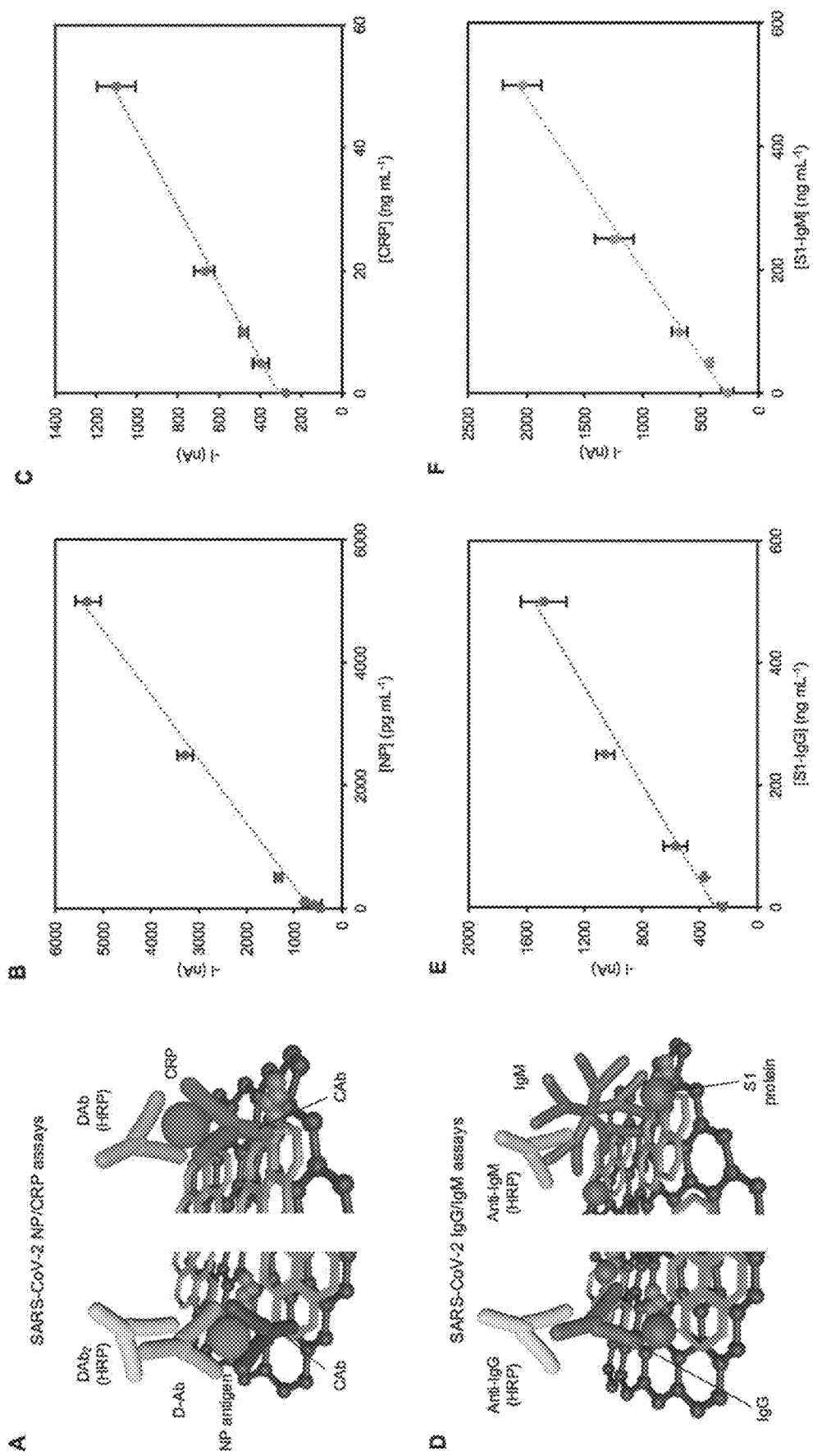
FIG. 4, panels A-E, shows investigation of the selectivity and multiplexed performance of the wireless SARS-CoV-2 methods of detection.

Example 3: Evaluation of Analytical Performance of the SARS-CoV-2 RapidPlex Platform The performance of each biosensor contained in the SARS-CoV-2 RapidPlex was characterized in phosphate-buffered saline (PBS) solutions supplemented with 1.0% of bovine serum albumin (BSA) by measuring the amperometric readout in the presence of increased concentrations of NP, S1-IgG, S1-IgM, and CRP (FIG. 4). The selected strategies for NP viral antigen and CRP proteins are based on double sandwich and sandwich configurations, respectively, as illustrated in FIG. 4A. The sandwich-based immunoassays for antigen detection are, in general, highly sensitive due to the involvement of two different antibodies as capture and detector entities. Variation of cathodic currents with the concentration for NP and CRP in buffered solutions are presented in FIGS. 4B and 4C, respectively. S1-IgG and S1-IgM were detected based on indirect immunoassays (FIG. 4D), which are considered highly suitable for detection of circulating macromolecules in antisera and other biofluids. FIGS. 4E and 4F show the calibration curves for S1 specific Ig determination (S1-IgG and S1-IgM, respectively) in buffered solutions. We did not observe significant slope variations between data obtained in properly diluted human serum and in buffered solutions for the determination of each target analyte; therefore, accurate quantification of the proposed target analytes can be carried out by conducting a simple interpolation of the cathodic readings obtained for each sample tested in the corresponding calibration curve constructed in buffered solution.

In addition, since diagnostic sensitivity and specificity of seroprevalence studies can be improved by using a mixture of antigenic proteins instead of a single protein, we modified graphene with a mixture of SARS-CoV-2 related antigens, NP and S1, to capture specific immunoglobulin isotypes against both antigens in the same WE. Thus, this methodology may be tailored for detecting isotype-specific IgG (or IgM) or a combination of both Ig isotypes in the same sensing surface to better capture total Ig concentration and thus increase assay sensitivity across the patient population.

Example 4: Investigation of the Selectivity and Multiplexed Performance of the SARS-CoV-2 RapidPlex Platform Human biofluids contain a complex and variable mixture of circulating molecules that may interfere with molecular sensing. In addition, negligible crosstalk between different working surfaces is an essential requirement to perform multiplexed detection readings accurately and meaningfully. Therefore, selectivity and crosstalk of the SARS-CoV-2 RapidPlex platform were evaluated. Amperometric readings obtained for each developed biosensor against non-target molecules are presented in FIG. 5A. We evaluated the specific binding for SARS-CoV-2 biomarkers in comparison to biomarkers of similar coronaviruses, including SARS-CoV and MERS-CoV. We observed no significant cross-reaction for NP, S1-IgG, S1-IgM and CRP assays in the presence of each tested interferent, including SARS-CoV-2 S1, SARS-CoV NP, SARS-CoV S1, and CRP (for NP assay), SARS-CoV-2 NP-IgG, SARS-CoV IgG, MERS-CoV IgG, S1-IgG, and negative controls containing mixtures of IgG and IgM against both MERS-CoV and SARS-CoV (for S1-IgG and S1-IgM assays), and BNP, NP, SARS-CoV NP and SARS-CoV S1 (for CRP assay), respectively. However, SARS-CoV NP viral antigen interferent provided a cathodic current corresponding to −80% of the raw current obtained for the detection of the specific NP antigen. Spike, envelope, and membrane SARS-CoV-2 proteins share 76-95% sequence identity with those of SARS-CoV. This percentage homology is reduced to 30-40% for MERS-CoV. Similarly, since SARS-CoV-2 NP is 90% identical to SARS-CoV NP, the interference observed from SARS-CoV NP antigen was expected. However, the lack of selectivity in this particular case is not a major concern due to the absence of new SARS-CoV cases detected recently; therefore, it can be inferred that this interference will not produce a barrier for selective SARS-CoV-2 NP determination in real samples. We further validated the use of amperometric-derived concentrations with absorbance-derived concentrations collected via ELISA. As it is presented in FIG. 5B, the results from our functionalized electrochemical biosensor were linearly correlated (r=0.991) with the results using the same reagents in a traditional ELISA protocol.

Figure 5:
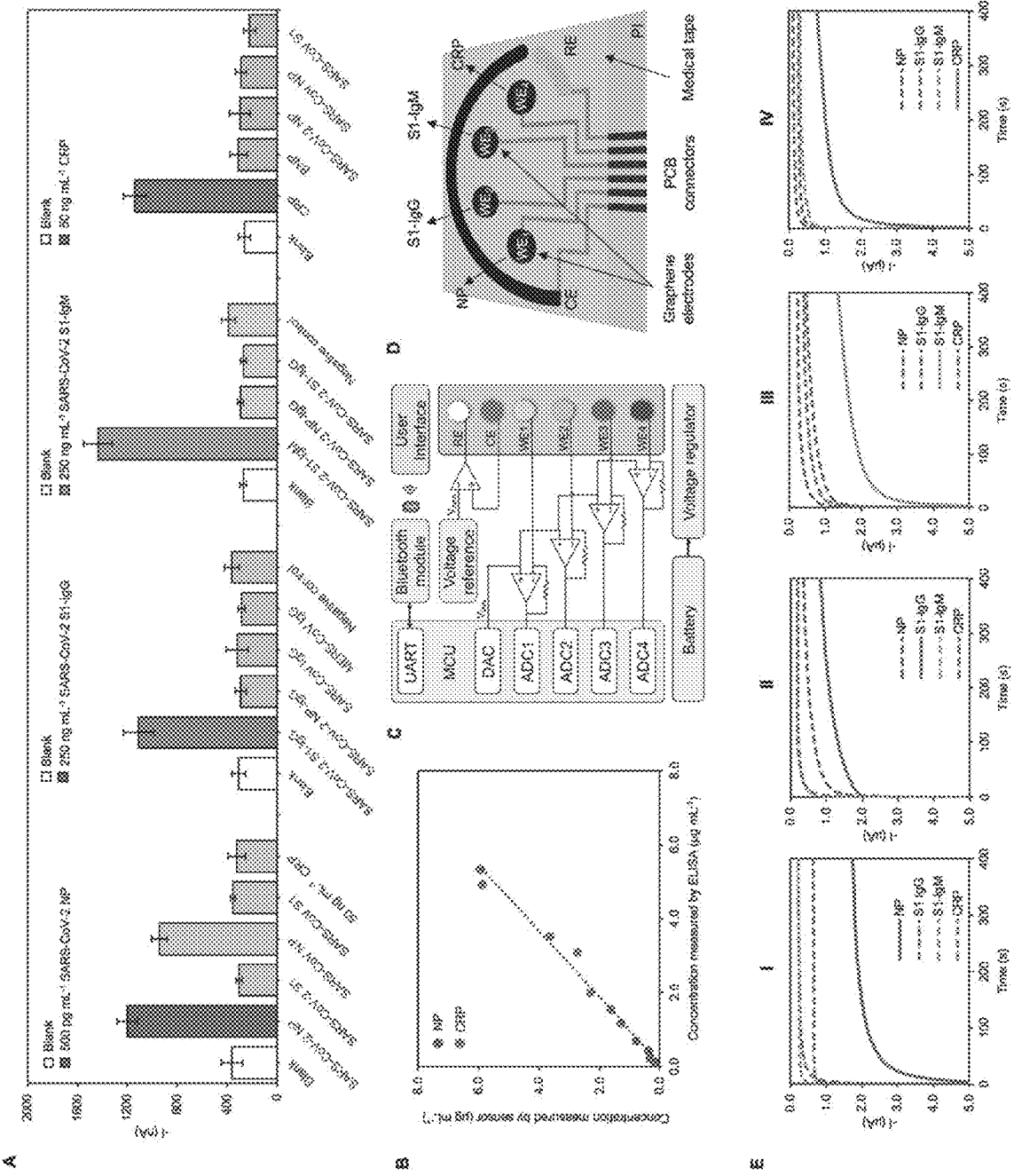
FIG. 5, panels A-F, shows application of the SARS-CoV-2 methods of detection in blood and saliva samples from COVID-19 positive and negative subjects.

Once the performance and selectivity of each constructed biosensor was individually and exhaustively evaluated, we demonstrate the multiplexing capabilities of the four-working-electrode (4WEs) graphene array device designed with a Ag/AgCl RE and a graphene CE. The block diagrams showing the functional units that comprise the integrated electronic system is illustrated in FIGS. 5C and 5D. Amperometric readings from the four channels are concurrently taken and data is wirelessly transmitted to a user device over Bluetooth Low Energy. The electronic system, including the printed circuit board (PCB) and a lithium-ion polymer battery, is 20×35×7.3 mm in dimension. The compact device can perform amperometric measurements continuously for over 5 hours in a single charge.

With the objective of demonstrating the utility of our SARS-CoV-2 RapidPlex array for multiplexed and simultaneous quantification of selected target molecules, we evaluated the potential cross-reaction resulting from the diffusion of signal substances between adjacent immunosurfaces. For this, each of the four conveniently functionalized working surfaces were incubated with buffered solutions containing significantly high concentration of each of the selected targets, followed by the corresponding detector receptors in each case. The absence of cross-talk between the adjacent working electrodes is verified from the experimental readings in buffered solutions containing 1.0 ng mL$^{-1}$ NP antigen (I), 250 ng mL$^{-1}$ S1 specific IgG (II) and—IgM (III), and 50 ng mL$^{-1}$ CRP (IV) (FIG. 5E). As envisaged, significantly higher signal was obtained when each target was specifically captured and further labeled by its tracer antibody in the corresponding functionalized immunosurface. These results, in conjunction with those from FIG. 5A demonstrate the feasibility of the developed SARS-CoV-2 RapidPlex platform for fast, selective and reliable determination of NP, S1-IgG and S1-IgM isotypes, and CRP in one single experiment. It should be noted that since IgG and IgM have similar binding mechanisms to viral antigens and individual quantification of Igs require no mixing of the specific detector labels, individual droplets were used on IgG and IgM sensing electrodes during modification and labelling.

Example 5: Detection of SARS-CoV-2 Related Selected Targets Human Biospecimens

Figure 6:
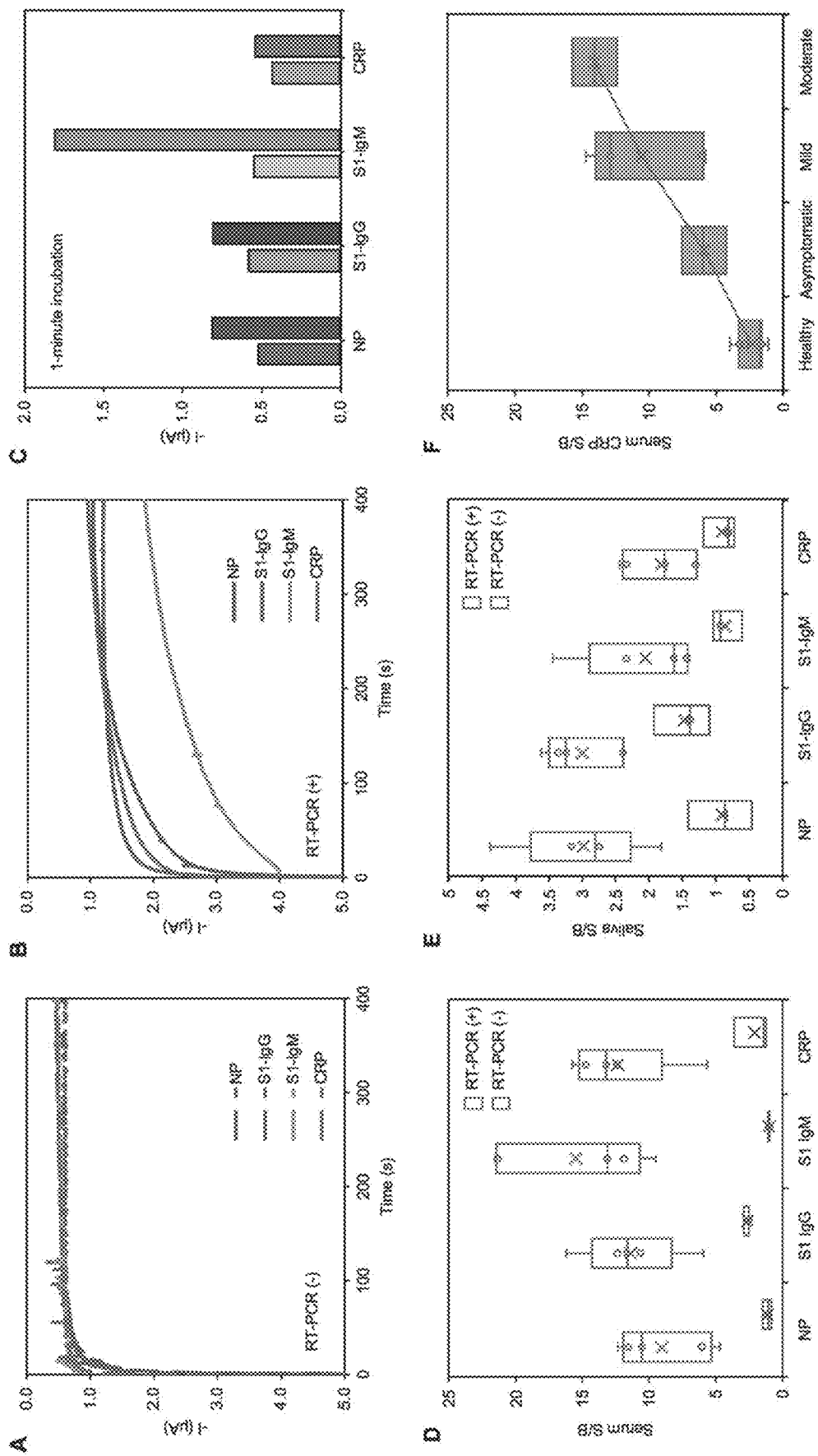
FIG. 6, panels A-B, shows characterization of the direct and oriented protein immobilization of SARS-CoV-2 antigenic protein for detection of specific IgG or IgM isotypes.

To prove the real utility of the present disclosure in a more complex and real scenario, we evaluated the multiplexed capabilities of SARS-CoV-2 RapidPlex in representative serum samples from COVID-19 RT-PCR negative and positive subjects. Sensor data from the serum samples of a RT-PCR negative patient (FIG. 6A) and a RT-PCR positive patient (FIG. 6B) show minimal cross-talk in a real and complex sample matrix, indicating the efficient functionality of SARS-CoV-2 RapidPlex to simultaneously differentiate the overexpressed presence of SARS-CoV-2 related biomarkers in COVID-19 positive specimens. Moreover, the SARS-CoV-2 RapidPlex device is able to provide significant positive readings for all biomarkers after incubating the COVID-19 positive serum sample for just 1 minute (FIG. 6C). The maintained high signal in positive patient samples demonstrates the great potential in future translation of the SARS-CoV-2 RapidPlex device as an ultra-fast POC remote diagnostic tool.

Results from FIGS. 6D and 6E corroborate that, as expected, compared to RT-PCR negative subjects, RT-PCR positive COVID-19 patients show significantly elevated levels of the selected biomarkers in both serum and saliva samples, with median SB ratios of 10.53, 11.62, 10.67 and 12.39 in serum, and 2.81, 3.24, 1.62, and 1.76 in saliva, for NP, S1-IgG, S1-IgM, and CRP, respectively. This proves the real utility for the accurate evaluation of the COVID-19 biomarkers in biofluids using the disclosed biosensors. In particular, the observed significant presence of COVID-19 biomarkers in saliva demonstrates the great utility of this biofluid as a valuable source for non-invasively diagnosing and monitoring SARS-CoV-2 infection.

Taken together, comparing the levels of the selected SARS-CoV-2 biomarkers of a patient to the selected SARS-CoV-2 biomarkers of a healthy individual, may identify numerous expected outcomes as illustrated in Table 1.

TABLE 1

A Patient's SARS-CoV-2 Infection Status Provided by the SARS-CoV-2 RapidPlex

| Viral Antigen | IgM | IgG | CRP | Expected Outcome |
|---|---|---|---|---|
| − | − | − | − | Vulnerable to infection |
| + | +/− | − | − | Early infection, prior to symptoms |
| + | + | + | − | Asymptomatic carrier |
| + | + | + | + | Symptomatic infected patient |
| − | +/− | + | − | Recovered patient, no longer vulnerable |
| − | − | − | + | Inflammation/infection not due to SARS-CoV-2 |

With the aim to confirm the relationship between the levels of inflammatory biomarkers involved in the cytokine storm directly associated with disease progression, severity, and outcome in COVID-19, we evaluated the variation of serum CRP levels in RT-PCR negative subjects (n=7) and RT-PCR positive COVID-19 patients who were classified clinically according to disease severity as asymptomatic (n=2), mild (n=5), and moderate (n=2). As shown in FIG. 6F, we observed a positive association between CRP concentration and COVID-19 symptom severity grade.

Future clinical testing using paired saliva and serum samples over the course of the infection is required to determine the relationship between saliva and serum concentrations and validate the utility of our platform in identifying and monitoring severity-specific COVID-19 (Table 1).

Example 6: Fabrication of Multiplex Array Electrode

For four channel graphene biosensor fabrication, a PI film was attached onto a supporting substrate in a 50 W $CO_2$ laser cutter (Universal Laser System VLS3.50). Selected laser-cutting parameters were: Power 8.0%, Speed 15%, Points Per Inch (PPI) 1000, in raster mode and at focused height. Ag/AgCl reference electrodes (RE) were fabricated by electrodeposition in 40 μL of a mixture solution containing silver nitrate, sodium thiosulfate, and sodium bisulfite (final concentrations 250 mM, 750 mM and 500 mM, respectively) for 100 seconds at −0.2 mA, followed by drop-casting 20 μL-aliquot of $FeCl_3$ for 1 minute.

Example 7: Functionalization of Multiplex Biosensing Platform and Electrochemical Readout 10 μL-aliquot of 5.0 mM PBA in DMF was drop-casted on the graphene surface and incubated for 2 hours at room temperature in a humid chamber. After rinsing with DMF, IPA, deionized (DI) water and drying under air flow, electrodes were incubated with 10 μL of a mixture solution containing 0.4 M EDC and 0.1 M Sulfo-NHS in 0.025 M IVIES (pH 6.5) for 35 minutes at room temperature under humid ambient conditions. Specific antibodies or coating protein were covalently attached onto activated surface by drop-casting 5.0 μL of the specific reagent (250 μg mL$^{-1}$ for S1-IgG, S1-IgM and CRP, or 50× dilution for NP, in 0.01 M phosphate-buffered saline (PBS, pH 7.4)) and incubated for 3 hours at room temperature, followed by 90 minutes blocking step with 2.0% BSA prepared in 0.01 M PBS. Subsequently, 10 μL of the corresponding target analyte prepared in 0.01 M PBS containing 1.0% BSA was incubated for 1- or 10 minutes at room temperature and, after one washing step with PBS, corresponding detector antibody (HRP labeled or unlabeled) (250× dilution for NP, 2.0 μg mL$^{-1}$ for S1-IgG and S1-IgM, and 1.0 μg mL$^{-1}$ for CRP) in 0.01 M PBS containing 1.0% BSA was incubated for 5 minutes at room temperature. In the case of NP assay, after incubating detector antibody and performing corresponding washing step with PBS, 10 μL of 1.0 μg mL$^{-1}$ HRP-goat anti rabbit IgG prepared in 0.01 M PBS containing 1.0% BSA was incubated for 5 minutes at room temperature. For each type of developed assay, amperometric readings were registered at −0.2 V (vs. Ag/AgCl) in 0.05 M sodium phosphate buffer (pH 6.0) containing 2.0 mM HQ. The readout signal was obtained in presence of 1.0 mM $H_2O_2$.

Example 8: Electrochemical and Microscopic Characterization of Multiplexed Biosensing Platform Amperometry, open circuit potential-electrochemical impedance spectroscopy (OCP-EIS), cyclic voltammetry (CV), and differential pulse voltammetry (DPV) were carried out on a CHI820 electrochemical station. The electrochemical setup comprised laser-induced graphene electrodes (LGEs) as the working electrodes (WEs), a platinum wire as the counter electrode (CE), and a commercial Ag/AgCl electrode as the reference electrode (RE).

For each type of proposed assay, surface modification after each step was electrochemically characterized by DPV and OCP-EIS. Corresponding readings by means of each technique were carried out in 0.01 M PBS (pH 7.4) containing 2.0 mM of $K_4Fe(CN)_6/K_3Fe(CN)_6$ (1:1) and under the followed detailed conditions: potential range, −0.2 and 0.6 V; pulse width, 0.2 s; incremental potential, 4 mV; amplitude, 50 mV; frequency range, 0.1-106 Hz; amplitude, 5 mV. Graphene functionalization methods were evaluated for both CRP and SARS-CoV-2 specific IgG assays, by comparing current responses obtained after developing each assay on both PBA and PPA-graphene, in the absence and in the presence of each of the corresponding target biomolecules (tested levels were 50 ng mL$^{-1}$ for CRP and 500 ng mL$^{-1}$ for SARS-CoV-2 specific IgG). Selectivity study was carried out by incubating corresponding interferential non-target molecules on the previously functionalized PBA-graphene. Concentration levels assayed for each interferent were the same (or even higher) than the concentration of the target molecule in each case. Amperometric signals obtained for each interferent tested were compared to the current signals obtained in the absence and in the presence of the corresponding target analyte for each type of assay.

To characterize the morphology and material properties before and after surface modification with PBA, SEM images of graphene electrodes were obtained by focused ion beam SEM (FIB-SEM, FEI Nova 600 NanoLab).

Example 9: Design and Fabrication of Electronic System for the Multiplex Platform The 4 channel chronoamperometric measurements were performed by a custom PCB-based wireless potentiostat. An Arm Cortex-M4 microcontroller (STM32L432KC; STMicroelectronics), and a Bluetooth module (SPBT3.0DP2; STMicroelectronics) were used for potentiostat control and wireless communication. A single operational amplifier (AD8605; Analog Devices) is used as the control amplifier, and a quad operational amplifier (AD8608; Analog Devices) is used as a four transimpedance amplifier to construct the potentiostat loop. A series voltage reference (ISL60002; Renesas Electronics) and the MCU's built-in digital to analog converter (DAC) were used to generate the voltage bias across the reference and working electrodes. 4 MCU built-in analog-to-digital converter (ADC) channels were used to concurrently acquire the measurements.

Example 10: Subjects and Procedures

In compliance with the protocols approved by the Institutional Review Board (no. 19-089417-292-A2) at the California Institute of Technology (Caltech), the performance of SARS-CoV-2 RapidPlex was evaluated in human serum and saliva samples from healthy and confirmed COVID-19 infected patients. Serum samples from 10 RT-PCR and IgG/IgM serology confirmed COVID-19 patients (age range 24-77 years) and 7 healthy subjects (age range 18-65 years) were purchased from BioIVT and Ray Biotech. Saliva samples from 5 RT-PCR and IgG/IgM serology test confirmed COVID-19 patients (age range 28-46 years) were purchased from BioIVT. 3 healthy saliva samples were used from preexisting stocks collected from volunteers prior to the pandemic. After receiving, serum and saliva samples were stored at −80° C. until required for its analysis. To perform the analysis of NP, CRP, S1-IgG and S1-IgM, no sample treatment was required for both serum and saliva samples; a simple dilution with 0.01 M PBS containing 1.0% BSA was performed prior to analysis.

Example 11: Determination of SARS-CoV-2 Related Selected Targets Molecules in Serum and Saliva Samples NP antigen, CRP, and S1-IgG and S1-IgM isotypes were analyzed in commercial serum and saliva samples from RT-PCR COVID-19 confirmed positive patients ($n_{serum}=10$; $n_{saliva}=5$) and healthy subjects ($n_{serum}=7$; $n_{saliva}=3$). After 100- and 5× dilution of corresponding serum and saliva samples in PBS with 1.0% BSA, respectively, 10 μL-aliquot was incubated in each WE for the corresponding time (1 or 10 minutes) at room temperature. After washing step with PBS buffer, corresponding detector reagents were incubated in each WE for 5 minutes and subsequent detection was performed. Comparison of sensor performance in buffer and diluted body fluids from healthy subjects spiked with increasing concentrations of target molecule was performed using CRP as a model molecule. We did not observe significant differences between slopes obtained both in PBS+1.0% BSA buffered solutions and diluted specimens (data not shown).

Example 12: Validation of Human Samples with the Gold Standard ELISA

ELISA tests for S1-IgG, CRP, and NP (selected as model targets) were performed in an accuSkan FC Filter-Based Microplate Photometer at a detection wavelength of 450 nm according to the manufacturer's instructions. In brief, plates were coated for 3 hours, shaking at 37° C., with 4.0 μg mL$^{-1}$ of the corresponding capture receptor in each case and blocked with PBS containing 1.0% BSA for 2 hours, shaking at 37° C., standards (or properly diluted samples), were added to coated microtiter plate wells and incubated for 2 hours, shaking at 37° C. Next, corresponding HRP-labeled detector antibody was incubated for 30 minutes at room temperature. Finally, 100 μL of 3,3 ',5,5'-tetramethylbenzidine (TMB) substrate was incubated for 15 minutes, and absorbance values were measured immediately after addition of 25 μL of 1 M $H_2SO_4$ in each well. Three washings with PBS containing 1.0% BSA were performed after each modification step.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A biosensor for detecting SARS-CoV-2 biological markers, comprising:
   (a) a microfluidics layer comprising:
      (i) a first surface configured to receive a biological sample;
      (ii) a second surface configured to directly and fluidically deliver a biological sample for analysis; and
      (iii) microchannels transversely oriented to transport a biological sample from the first surface to and through the second surface;
   (b) a multimodal sensing layer fluidically coupled to the second surface of the microfluidics layer to receive the biological sample directly from the microchannels comprising:
      (i) a counter electrode;
      (ii) a reference electrode; and
      (iii) a working electrode comprising a first detection protein configured to capture a first SARS-CoV-2 biomarker and a second detection protein configured to capture a second SARS-CoV-2 biomarker,
      (iv) wherein the working electrode is configured to singularly detect a measurement of an electrical property corresponding to the first and/or second SARS-CoV-2 biomarkers present in the biological sample; and
   (c) a logic circuit comprising a processor and a non-transitory memory with computer executable instructions embedded thereon wherein the logic circuit is electrically coupled to the electrodes and the computer executable instructions cause the processor to identify the electrical properties detected with the working electrode, the electrical properties indicating the first and/or second SARS-CoV-2 biomarkers present in the biological sample.

2. The biosensor of claim 1, wherein the working electrode comprises catalytically active substrate.

3. The biosensor of claim 2, wherein the catalytically active substrate is graphene.

4. The biosensor of claim 1, wherein the counter electrode is a graphene counter electrode.

5. The biosensor of claim 1, wherein the reference electrode is a Ag/AgCl reference electrode.

6. The biosensor of claim 1, wherein the electrical property is an electrical current.

7. The biosensor of claim 1, wherein the electrical property is an electrical voltage.

8. The biosensor of claim 1, wherein the electrical property is an electrical impedance.

9. The biosensor of claim 1, wherein the computer executable instructions cause the processor to generate an indication identifying the presence of the first and/or second SARS-CoV-2 biomarker based on the electrical property detected with the working electrode.

10. The biosensor of claim 1, wherein the working electrode further comprises a third detection protein configured to capture a third SARS-CoV-2 biomarker.

11. The biosensor of claim 10, wherein the working electrode further comprises a fourth detection protein configured to capture a fourth SARS-CoV-2 biomarker.

12. The biosensor of claim 1, further comprising a display, wherein the computer executable instructions further cause the processor to output the indication identifying the presence and/or level of the first and/or second SARS-CoV-2 biomarkers to the display.

13. The biosensor of claim 1, further comprising a wireless transmitter, wherein the computer executable instructions further cause the processor to output the indication identifying the presence and/or level of the first and/or second SARS-CoV-2 biomarkers to the wireless transmitter, and wherein the wireless transmitter wirelessly transmits the indication identifying the presence and/or level of the first and/or second SARS-CoV-2 biomarkers to a user device.

14. The biosensor of claim 13, wherein the wireless transmitter wirelessly transmits to a user device over Bluetooth Low Energy.

15. The biosensor of claim 1, wherein the first and second detection proteins configured to capture the first and second SARS-CoV-2 biomarkers are immobilized on the working electrode.

16. The biosensor of claim 1, wherein the multimodal sensing layer comprises a polymer.

17. The biosensor of claim 1, wherein the working electrode comprises one or more uniform redox probe, and the uniform redox probe is deposited on a surface of the working electrode.

* * * * *